US005769086A

United States Patent [19]
Ritchart et al.

[11] Patent Number: 5,769,086
[45] Date of Patent: Jun. 23, 1998

[54] CONTROL SYSTEM AND METHOD FOR AUTOMATED BIOPSY DEVICE

[75] Inventors: Mark A. Ritchart, Murrieta; Fred H. Burbank, San Juan Capistrano, both of Calif.

[73] Assignee: Biopsys Medical, Inc., Irvine, Calif.

[21] Appl. No.: 568,143

[22] Filed: Dec. 6, 1995

[51] Int. Cl.$^6$ .................................................. A61B 10/00
[52] U.S. Cl. ........................................................ 128/753
[58] Field of Search ........................ 128/749, 751–755; 600/105

[56] References Cited

U.S. PATENT DOCUMENTS

| | | | |
|---|---|---|---|
| 4,702,260 | 10/1987 | Wang | 128/753 |
| 5,415,169 | 5/1995 | Siczek et al. | 128/754 |
| 5,526,822 | 6/1996 | Burbank et al. | 128/754 |
| 5,584,292 | 12/1996 | Cheung | 128/653.1 |
| 5,602,449 | 2/1997 | Krause et al. | 128/755 |

FOREIGN PATENT DOCUMENTS

| | | |
|---|---|---|
| 0378692 | 7/1990 | European Pat. Off. . |
| 0442851 | 8/1991 | European Pat. Off. . |
| 9314707 | 8/1993 | WIPO . |

*Primary Examiner*—Max Hindenburg
*Attorney, Agent, or Firm*—Donald E. Stout

[57] ABSTRACT

An automatic control system for a vacuum-assisted automatic core biopsy device (10) is provided, wherein the automatic core biopsy device (10) comprises a housing (12), out of which extends a needle assembly (14) including a hollow outer piercing needle (16), an inner cutter (18) having a lumen (20), a probe housing (22), and a tissue receiving notch (24). The automatic control system (92) is computerized to move the hollow outer piercing needle (16) automatically to the target tissue lesion, as was true in the prior art, but also is programmed to automatically control the rotational orientation of the piercing needle (16), and its associated tissue receiving notch (24), as well as the axial positioning and rotation of the cutting cannula (18). Consequently, a clinician user need only mark the desired locations within the target location from which tissue samples are desired and the automatic control system will operate the device to retrieve samples from the marked locations.

27 Claims, 7 Drawing Sheets

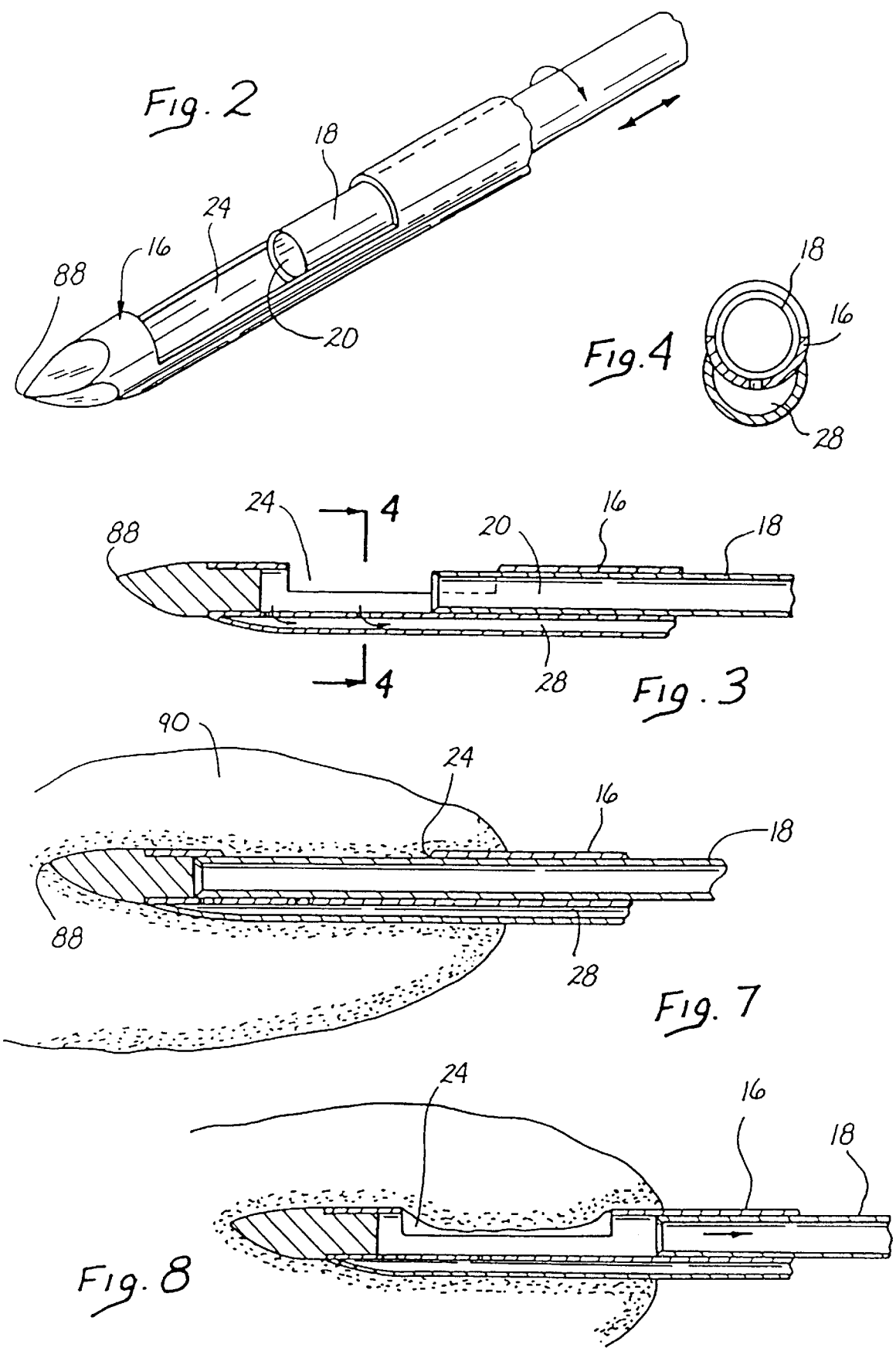

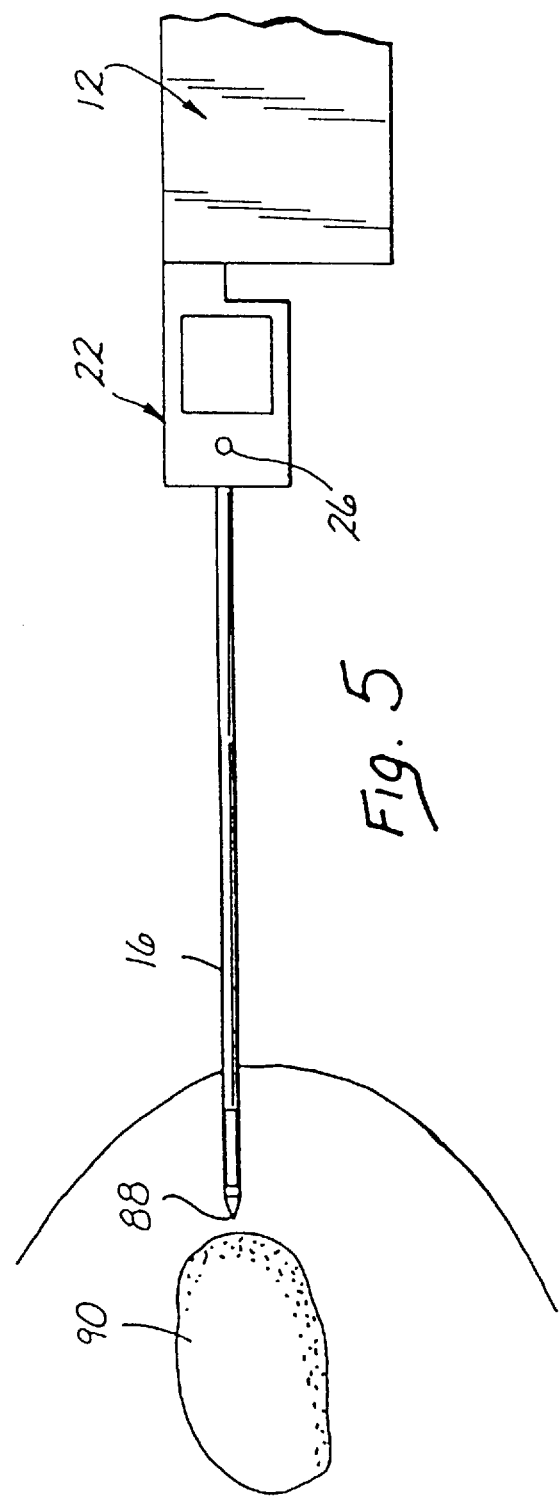
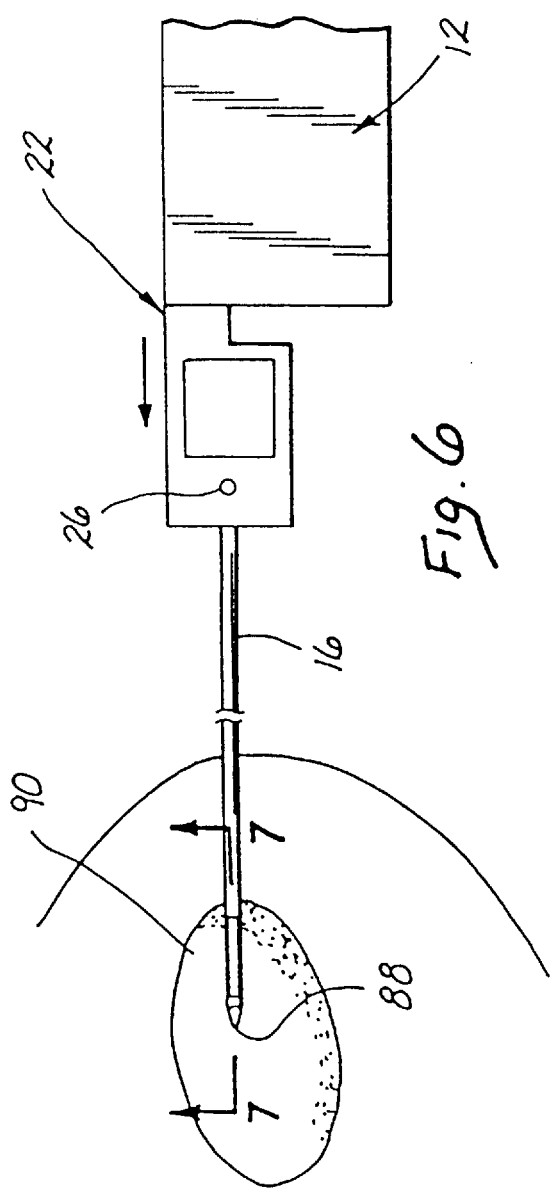

CONTROL SYSTEM AND METHOD FOR AUTOMATED BIOPSY DEVICE

CROSS-REFERENCE TO RELATED APPLICATIONS

This application is related to co-pending applications Ser. No. 08/217,246, entitled *Method and Apparatus for Automated Biopsy and Collection of Soft Tissue* and filed Mar. 24, 1994 and Ser. No. 08/386,941, entitled *Methods and Devices for Automated Biopsy and Collection of Soft Tissue* and filed Feb. 10, 1995. Both of these applications are herein expressly incorporated by reference.

FIELD OF THE INVENTION

The present invention relates to methods and devices for tissue sampling, and more specifically to improved control systems and methods for biopsy instruments.

BACKGROUND OF THE INVENTION

It is often desirable and frequently necessary to sample or test a portion of tissue from humans and other animals, particularly in the diagnosis and treatment of patients with cancerous tumors, pre-malignant conditions, and other diseases and disorders. Typically, in the case of cancer, when the physician establishes by means of procedures such as palpation, x-ray, or ultrasound imaging that suspicious circumstances exist, a biopsy is performed to determine whether the cells are cancerous. Biopsy may be done by an open or percutaneous technique. Open biopsy, which is an invasive surgical procedure using a scalpel and involving direct vision of the target area, removes the entire mass (excisional biopsy) or a part of the mass (incisional biopsy). percutaneous biopsy, on the other hand, is usually done with a needle-like instrument through a relatively small incision, blindly or with the aid of an artificial imaging device, and may be either a fine needle aspiration (FNA) or a core biopsy. In FNA biopsy, individual cells or clusters of cells are obtained for cytologic examination and may be prepared such as in a Papanicolaou smear. In core biopsy, as the term suggests, a core or fragment of tissue is obtained for histologic examination which may be done via a frozen section or paraffin section.

The type of biopsy utilized depends in large part on circumstances present with respect to the patient, and no single procedure is ideal for all cases. However, core biopsy is extremely useful in a number of conditions and is being used more frequently by the medical profession.

Two types of image guided percutaneous core breast biopsy instruments are presently available. One such instrument is a spring-powered single-use device, such as the BIOPTY® gun, available from C. R. Bard, Inc. Such a gun is shown and described in U.S. Pat. Nos. 4,699,154 and 4,944,308, as well as in U.S. Reissued Pat. No. Re. 34,056, all of which are herein expressly incorporated by reference. The advantages and disadvantages of this type of instrument are discussed in detail in co-pending application Ser. No. 08/386,941. The second type of image guided percutaneous core breast biopsy instrument currently available is a vacuum-assisted automatic core biopsy device. One such successful biopsy gun is shown and disclosed in the previously referenced related parent applications Ser. No. 08/217, 246 and Ser. No. 08/386,941, both of which are commonly owned by the assignee of the present application. This gun includes a piercing cannula and a cutting cannula and has the capability to active capture tissue prior to cutting the tissue. Mechanisms are included for rotationally orienting the piercing cannula, which has a tissue capture notch near the distal end thereof, so that the notch is in a desired angular orientation for receiving a tissue sample. Additional mechanisms permit the cutting cannula to travel axially, so that it may be retracted and advanced as desired, and rotationally, in order to assist the cutting process. Active capture allows for sampling through non-homogeneous tissues, meaning that the device is equally capable of cutting through hard and soft tissue. The gun also includes means to direct and position the cutting chamber in arbitrary positions about and along its longitudinal axis, means for rapid and atraumatic removal of an arbitrary number of core samples with only a single needle insertion into the body and organ, and means for coding and decoding the location from which the samples were obtained. Together, these capabilities allow for more complete sampling of large lesions and for the complete removal of small lesions. This type of instrument has been very successful in permitting the obtainment of a plurality of tissue samples from different locations with only a single needle insertion, as well as in obtaining high quality samples in a manner which does not require direct handling of the samples by the operator.

Previously, vacuum-assisted automatic core biopsy devices of the type disclosed in the aforementioned '246 and '941 patent applications have been manually operated once the piercing needle of the device is located as desired adjacent to a target lesion. Thus, the mechanisms for rotating the piercing cannula, and for rotating and axially translating the cutting cannula, have typically been initiated by manually actuating a switch to activate a driving motor. It would be a significant advantage, however, to be able to automatically control all aspects of the tissue retrieval process, including control of the cutter, aspiration, and orientation of the tissue receiving notch, so that the user is free to entirely concentrate on the medical procedure itself and in order to improve the accuracy and efficiency of the procedure.

SUMMARY OF THE INVENTION

This invention accomplishes the aforementioned objective by providing an automatic control system for a vacuum-assisted automatic core biopsy device. With the inventive system, not only is the piercing needle automatically directed to the target tissue lesion, as was true in the prior art, but the rotational orientation of the piercing needle, and its associated tissue receiving notch, as well as the axial positioning and rotation of the cutting cannula, are automatically controlled as well. Consequently, a clinician user need only mark the desired locations within the target location from which tissue samples are desired and the automatic control system will operate the device to retrieve samples from the marked locations.

More particularly, an automatic biopsy device is provided which comprises a first elongate cannula having a distal end for entering tissue and a notch located proximally of the distal end for receiving a portion of the tissue which is positioned adjacent to the notch. A second elongate cannula having a sharpened distal end is disposed coaxially with the first cannula, so that the second cannula is slidable along the first cannula for cutting the portion of tissue protruding into the notch when the second cannula slides past the notch. This action causes the portion of cut tissue to be deposited within the first elongate cannula proximal to the first cannula distal end.

Also included in the inventive device is a first driving mechanism for rotationally driving the first cannula about its longitudinal axis, so that the notch may be rotated to any desired orientation for sampling tissue from different locations about the first cannula, and a second driving mechanism for moving the second cannula relative to the first cannula A monitor having a screen for displaying a target lesion site to a user and a processor for receiving instructions from the user regarding regions of the target lesion from which tissue samples are to be taken also comprise part of the system.

Significantly, a controller, which may or may not comprise a part of the processor, is employed for receiving instructions from the processor and for automatically controlling the first driving mechanism to rotate the notch to a desired orientation for obtaining a tissue sample and the second driving mechanism to move the second cannula to cut the tissue sample so that it is deposited within the first cannula.

In another aspect of the invention, an automatic biopsy device is provided which comprises a hollow needle having a distal end and a tissue receiving notch and a cutter having a sharpened distal end and which is disposed coaxially within the hollow needle. Also included are a first driver for rotating the hollow needle to orient the tissue receiving notch in a desired radial orientation and a second driver for axially moving the cutter so that it is slidable along the hollow needle for cutting tissue protruding into the notch. A key feature of the invention is the provision of a processor for receiving instructions from a user related to desired portions of a target lesion to be sample and instructing a controller to automatically control each of the first and second drivers to move the hollow needle and the cutter in order to obtain the desired tissue lesion portions.

In yet another aspect of the invention, a method is disclosed for controlling an automatic biopsy device, wherein the device comprises a first elongate cannula having a distal end for entering tissue and a tissue-receiving notch, and a second elongate cannula having a sharpened distal end and disposed coaxially with the first cannula. The method comprises the steps of providing instructions as to the portions of the lesion from which tissue samples are desired by denoting on a computer monitor screen displaying a target lesion the portions to be sampled, transmitting the instructions to a processor, processing the instructions and transmitting instructions from the processor to a controller, and using the controller to automatically drive the first cannula to rotate to a desired notch position and to automatically drive the second cannula to cut tissue protruding into the notch, to thereby obtain a tissue sample. This procedure may be repeated as many times as desired to obtain a predetermined number of samples, so that the entire lesion is effectively sampled.

Two different approaches may be taken to providing instructions to the processor. In one embodiment, the user denotes on the monitor screen each specific point from which tissue samples should be taken to effectively sample the target lesion by "clicking on" the points with his mouse or other tracking device. Then, the coordinates of these points are transmitted by the processor to the controller in order to direct the device to obtain samples at each of these points. In the second embodiment, the user merely shades the portion from which tissue samples are to be taken (i.e. shades the target lesion) by dragging the screen cursor across the portion using his mouse. The processor then calculates the specific points from which tissue samples should be taken to effectively sample the entire shaded region and transmits the coordinates of these calculated points to the controller.

The invention, together with additional features and advantages thereof, may best be understood by reference to the following description taken in conjunction with the accompanying illustrative drawing.

BRIEF DESCRIPTION OF THE DRAWINGS

FIG. 2 is an enlarged perspective view of the portion of FIG. 1 delineated by the numeral 2;

FIG. 3 is a cross-sectional view of the needle assembly illustrated in FIG. 2;

FIG. 4 is a cross-sectional view taken along lines 4—4 of FIG. 3;

FIG. 5 is a schematic plan view, from the left side, of a portion of the needle assembly of the device illustrated in FIG. 1, showing the device before it penetrates a target lesion;

FIG. 6 is a schematic plan view similar to FIG. 5, showing the device after it has penetrated the target lesion, in a position to begin collecting tissue samples;

FIG. 7 is an enlarged cross-sectional view taken along lines 7—7 of FIG. 6;

FIG. 8 is an enlarged cross-sectional view similar to FIG. 7, illustrating the withdrawal of the cutter after insertion of the needle into the target lesion;

DESCRIPTION OF THE INVENTION

Figure 1:
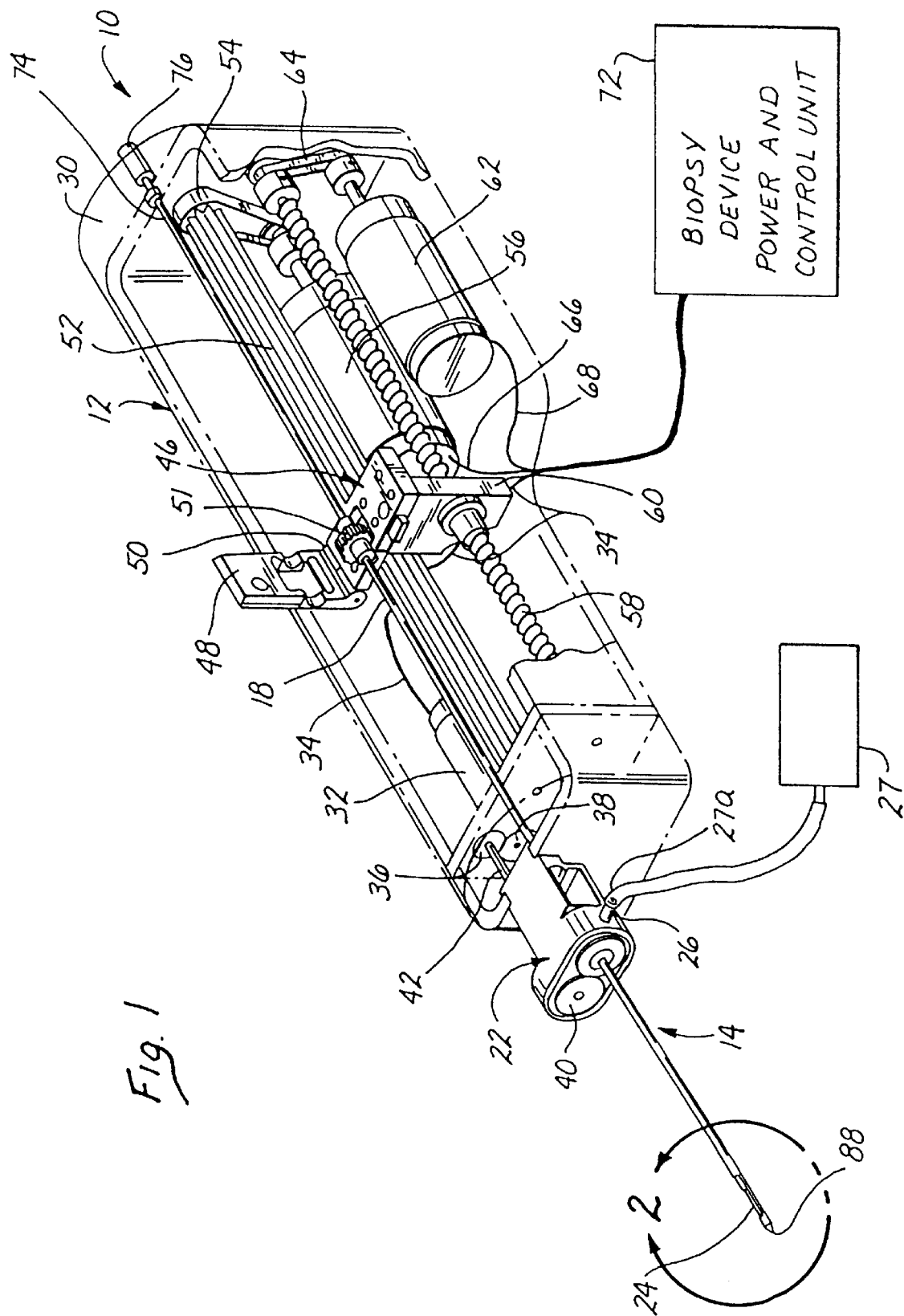
FIG. 1 is a perspective view of a preferred embodiment of an automatic core biopsy device, of the type shown and described in co-pending patent applications Ser. Nos. 08/217,246 and 08/386,941.

Referring now more particularly to FIGS. 1, 2 and 3, a preferred embodiment of an automatic core biopsy device 10, of the type disclosed in related patent applications Ser. Nos. 08/217,246 and 08/386,941 is illustrated. The illustrated biopsy instrument 10 comprises a housing 12, out of which extends a needle assembly or probe body 14. The probe body 14 includes a hollow outer piercing needle 16, an inner cutter 18 having a lumen 20 (FIG. 2), a probe housing 22, and a tissue receiving notch 24. An aspiration port 26 is adapted for attachment to a source of vacuum pressure 27 through a tube or tubing 27a, in order to aspirate the notch 24. Preferably, the vacuum is supplied through a separate vacuum lumen 28, but may alternatively or simultaneously be supplied directly through the lumens of the hollow outer piercing needle 16 and the inner cutter 18, respectively, if desired.

The housing 12 is illustrated with the lid 30 broken away in order to reveal the contents of the housing. Enclosed therein are the driving mechanisms and controls for operating the probe body 14. These mechanisms include a notch orientation drive system comprising a notch orientation motor 32 which is controlled and powered by a power/control cable 34. The notch orientation motor 32 drives a primary notch orientation gear 36 to rotate or oscillate through a notch orientation drive gear 38; the primary notch orientation gear 36 in turn driving a secondary notch orientation gear 40 to rotate or oscillate by means of a shaft 42. A notch orientation gear 44, driven by the secondary notch orientation gear 40, is adapted to rotate or oscillate the outer piercing needle 16 through a 360 degree arc, for the purpose of obtaining a plurality of tissue samples from various orientations, as will be described more fully hereinbelow.

In addition to the notch orientation drive system, the housing 12 includes a carriage assembly 46 for rotating, oscillating, retracting, and advancing the cutter 18. A carriage assembly cover/latch 48 is attached to the carriage assembly 46 by means of a hinge 50, about which the cover/latch 48 may be pivoted from its open position (shown in FIG. 1) to its closed position covering the carriage assembly. In the carriage assembly 46 is a cutter gear 51, which is driven by interengagement with a cutter power gear 52 to rotate or oscillate the cutter 18. The cutter power gear is driven to rotate or oscillate through a cutter gear drive belt 54 by a cutter drive motor 56. The carriage assembly 46 is threadedly attached to a ball screw gear 58 through a ball screw flange 60 for linear travel therealong, thereby enabling the cutter to be retracted and advanced as desired. The ball screw gear 58 is rotatably driven by means of a ball screw drive motor 62 through a ball screw drive belt 64. The cutter drive motor 56 and the ball screw drive motor 62 are each powered and controlled by a cutter gear drive power/control cable 66 and a ball screw drive motor power/control cable 68, respectively. All of the various motor power/control cables 34, 66, and 68 are in turn connected to a unit power/control cable 70 which connects the biopsy device 10 with a biopsy device power and control unit 72 (FIGS. 18 and 19) to be described in more detail hereinbelow.

Telescopically and coaxially arranged within the hollow outer piercing needle 16 and the inner cutter 18 is a knock-out pin 74. It is mounted from a knockout hub 76 to be stationary, and is preferably fabricated of stainless steel, but may also be constructed of other biocompatible materials, such as plastic. The pin 74 preferably is tubular, and the hub 76 serves as a secondary vacuum port which supplies the vacuum through the needle 16 and the cutter 18.

Figure 17:
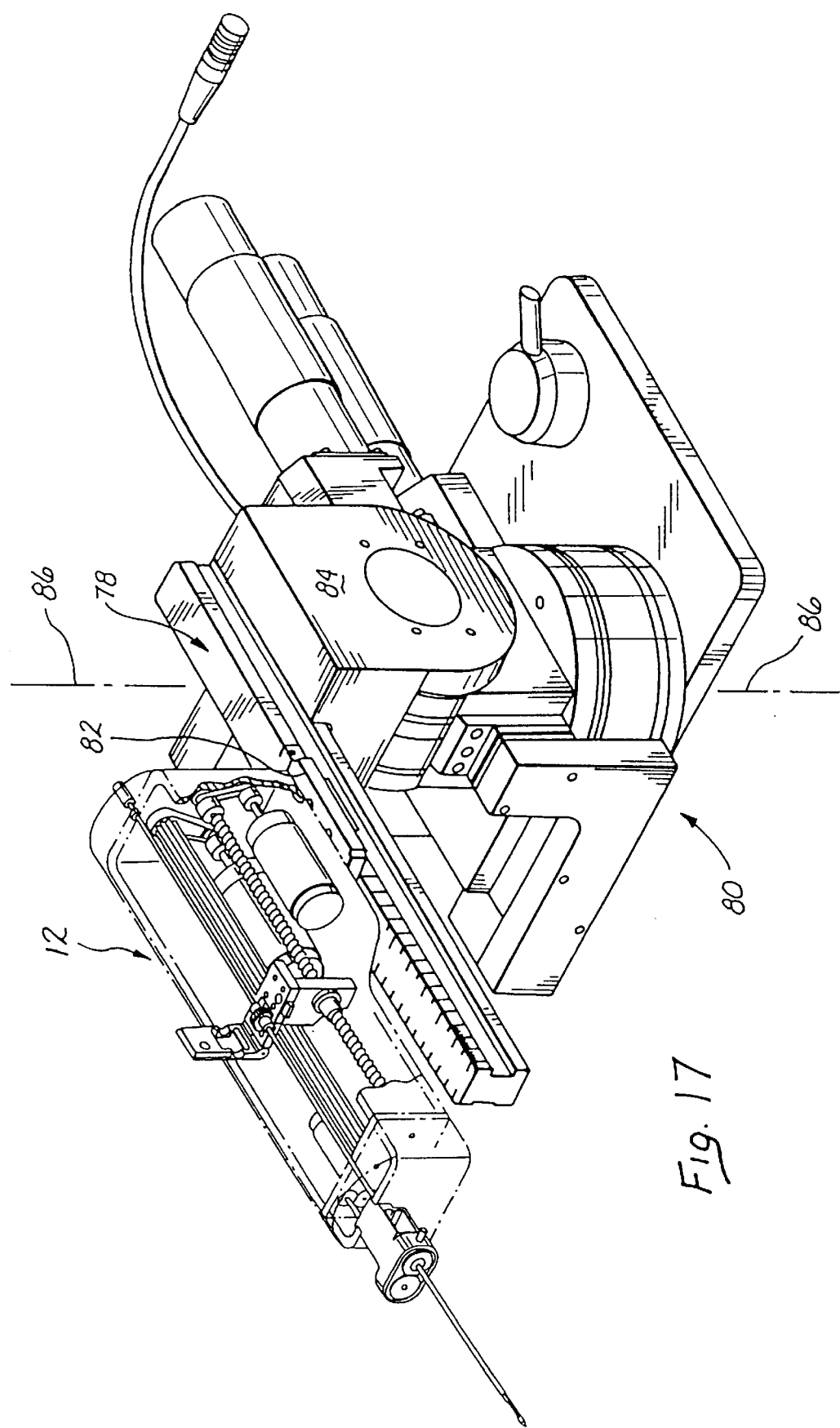
FIG. 17 is a perspective view of a motorized biopsy needle positioning mechanism employed in the inventive controller system for controlling the movement of the biopsy device shown in FIG. 1.

The biopsy instrument housing 12 is preferably mounted on a base which is adapted to mate with an I-beam rail 78 of a function arm 80 for a stereotactic imaging unit, as illustrated in FIG. 17. Of course, it may be modified and designed to match and mate with any of the various imaging units available in the industry, but one preferred unit shown in FIG. 17 is manufactured by Fischer Imaging Corporation of Denver, Colo., and is more fully described in U.S. Pat. No. 5,240,011 to Assa, herein expressly incorporated by reference. The punction arm 80 comprises a linear motor 82 on the rail 78, on which the biopsy instrument housing 12 is attached, which linear motor is disposed to travel linearly along the rail 78, thereby causing the housing 12 to likewise travel linearly as desired. The rail 78, in turn, is disposed on a gimbal housing 84, which is pivotable about a vertical axis 86 to provide rotational as well as translational control of the biopsy instrument.

A piercing mechanism (not shown) may also be housed in the housing 12 of the biopsy instrument 10, if desired, which is preferably spring-driven so that it may be "fired" to rapidly advance the entire probe housing distally, in order to locate the tip of the outer piercing needle 16 at the site from which one or more tissue samples are desired.

In operation, as described in the aforementioned co-pending applications, the point 88 of the needle 16 is first moved into position to pierce the lesion or selected tissue 90 which is to be sampled (FIGS. 5 and 6). The initial global position of the point 88 with respect to the tissue area being sampled is determined by the overall position of the biopsy instrument 10 with respect to the patient. This is accomplished in a manner well known in the art using the punction arm 80 of a known stereotactic guidance system, and one such preferred method for positioning the point 88 adjacent to the specific lesion region 90 to be sampled, as illustrated in FIG. 5, is described in the aforementioned Assa Patent No. 5,240,011.

Once the point 88 is adjacent to the specific lesion region to be sampled (FIG. 5), fine tuning of the location of the point 88 within the tissue sample (FIG. 6) is accomplished, in known fashion, by operating the linear motor 82 to thereby advance and retract the hollow outer piercing needle 16 along its axis. In some embodiments, a potential energy device, such as a spring, may be used to "fire" the point in a distal direction, to cause the needle to enter the lesion.

Figure 18:
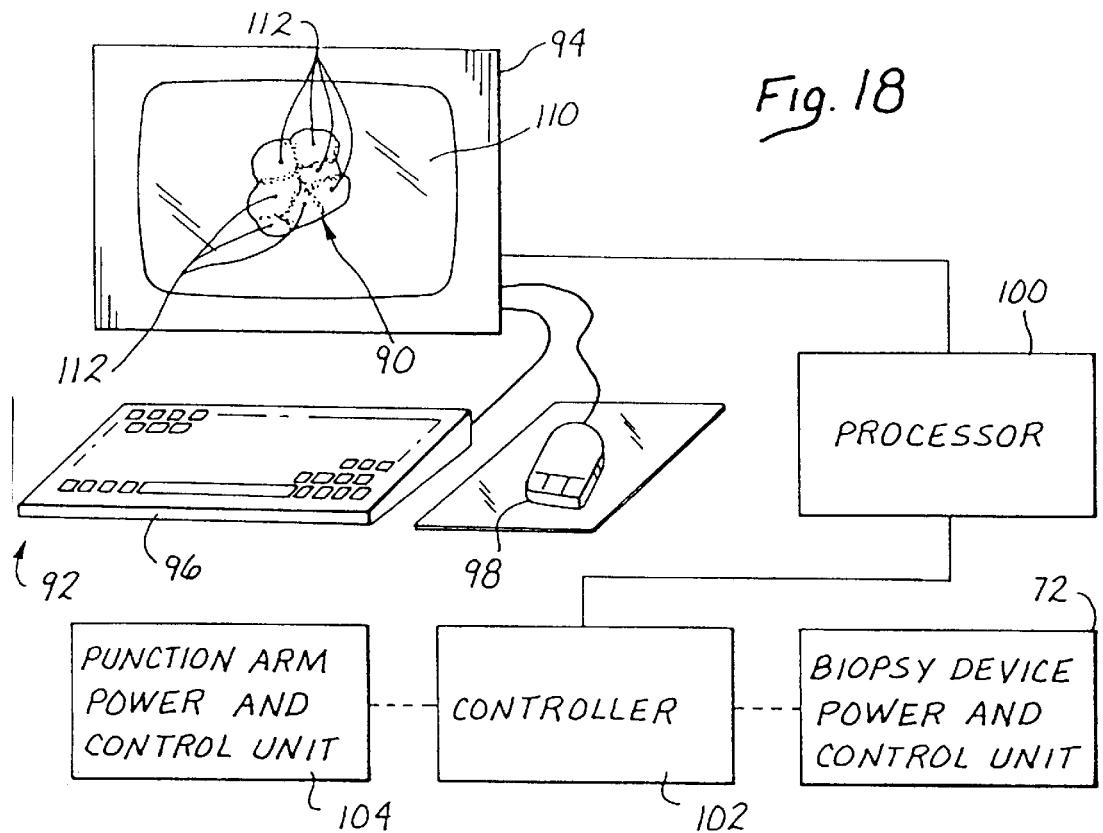
FIG. 18 is a schematic diagram showing a first inventive method for controlling the movement of the biopsy device shown in FIG. 1.
Figure 19:
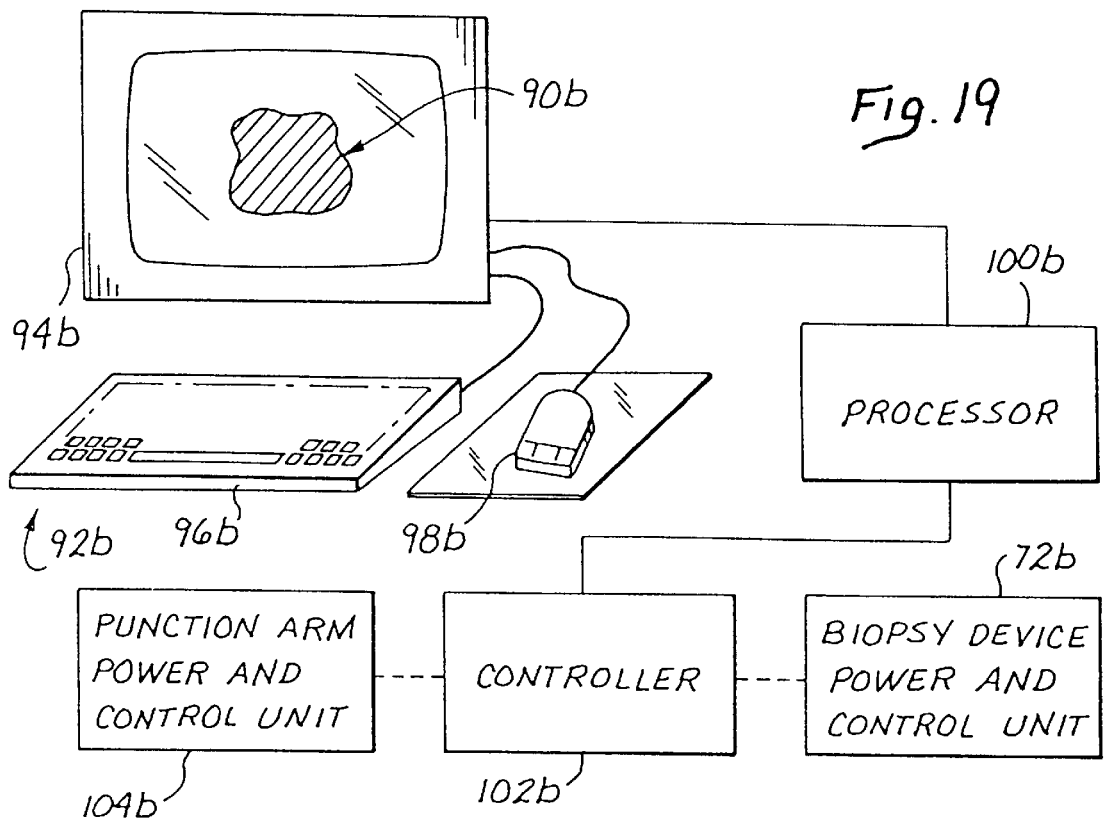
FIG. 19 is a schematic diagram showing a second inventive method for controlling the movement of the biopsy device shown in FIG. 1.

It is preferred that control of the punction arm 80 or equivalent device for moving the needle 16 relative to the lesion 90 is accomplished automatically, using a computerized control system 92 like that shown in FIGS. 18 and 19. The system 92 preferably includes a personal computer system, which includes a display monitor 94, a keyboard 96, a tracking device, such as a mouse 98, and a processor or CPU 100. A controller 102 is operatively connected to the processor 100. In the preferred embodiment the controller 102 is a relay device which is operatively connected to both the biopsy device power and control unit 72 and a punction arm power and control unit 104. Of course, many different system variants may be used, and it is expected that more alternatives will become available over time given the rapidly evolving technology in the control and computer fields. For example, it may in some instances be preferable to employ a controller 102 which is internal to the computer system, and perhaps integrated with the processor 100.

Movement of the needle 16 into position with respect to the target lesion 90, by moving the linear motor 82 of the punction arm 80, is initiated by a user in known fashion, as described in the aforementioned Assa patent, by, for example, employing a film digitizer and coordinates calculator (not shown) to digitize the target lesion 90 within the patient's breast and to then compute the spatial coordinates of the lesion. The computed spatial coordinates then appear on the display monitor 94, and the user employs the mouse 98 to automatically set the biopsy needle positioning mechanism 80 so that the biopsy needle 16 positioned thereon is precisely positioned for insertion to the lesion 90 by depressing appropriate keys on the hand controller or mouse 98. These instructions are relayed to the processor 100, which calculates the necessary coordinates for the desired needle point location and in turn instructs the controller 102 with respect to these coordinates. The controller 102 then instructs the punction arm power and control unit 104 to operate the punction arm 80 to move the linear motor 82 until the point 88 of the needle 16 is located at the calculated coordinates. Alternatively, the punction arm 80 may be manually controlled by using the mouse 98 to guide the needle to the desired entry location. In this instance, the coordinates of the cursor on the display screen as the mouse is moved to guide the cursor to the target location are directly relayed by the processor to the controller in order to instruct the punction arm power and control unit 104.

Of course, though a punction arm 80 is shown and described as the preferred means for moving the needle 16 to the location of the target lesion 90, many other equipment alternatives may be used to achieve the same end result. It may even be desirable in certain instances to maintain the needle 16 in a stationary position and to move the patient's target lesion to the location of the needle using a punction table or the like.

Now with particular reference to FIGS. 7–12, as seen in FIG. 7, the needle 16 is preferably advanced into the lesion 90 with the inner cutter 18 in its fully advanced position to close off the notch 24, thus preventing snagging and tearing of the tissue during slow linear movement of the needle 16. In accordance with this invention, the clinician user views an image of the target lesion 90 on a screen 10 of the display monitor 94, which is generated by suitable imaging equipment which digitizes it and presents it on the screen 110. As shown in FIG. 18, in one preferred embodiment, the user uses the tracking device or mouse 98 to "click" on or denote a plurality of desired points 112 within the lesion. These points 112 represent points from which tissue samples should be taken to effectively sample the entire target lesion. The processor 102 then transmits the locations of each of these specific points to the controller 104, which in turn instructs the biopsy device power and control unit 72 to operate the notch orientation motor 32 to drive the notch orientation gears so that the notch 24 may be positioned at a desired angular orientation by rotating the hollow outer piercing needle 16 about its longitudinal axis through a desired portion of a 360 degree arc, so that the samples are taken at the points within the lesion designated on the monitor screen 110 by the user. The control unit 72 is also instructed by the controller 102 to operate the ball screw drive motor 62 to rotate the ball screw gear 58 in a desired direction to advance or retract the cutter 18, depending upon the procedural step being performed.

Figure 9:
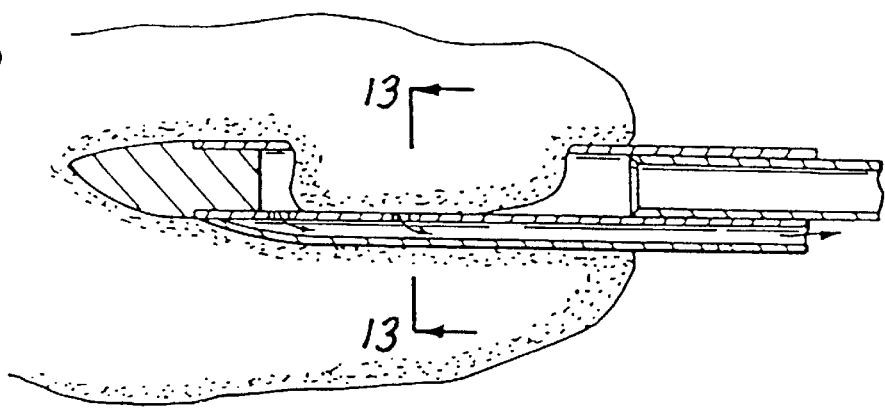
FIG. 9 is an enlarged cross-sectional view similar to FIG. 7, illustrating the prolapse of tissue into the tissue receiving port following the application of the vacuum pressure.

After the hollow outer piercing needle 16 has been positioned by the punction arm 80 at the precise location within the lesion 90 at which it is desired to obtain a tissue sample, the vacuum source 27 is actuated automatically by the controller 102, through the biopsy device power and control unit 72, to apply a vacuum to the aspiration port 26 in the probe housing 22 (FIG. 1) through the vacuum tube 27a as the cutter is retracted proximally (FIGS. 8 and 9). As a result, a region of low pressure is generated within the hollow outer piercing needle 16 in the vicinity of the notch 24, and through the vacuum lumen 28. This facilitates the prolapse of tissue immediately adjacent to the notch 24 into the interior of the hollow outer piercing needle 16.

Figure 10:
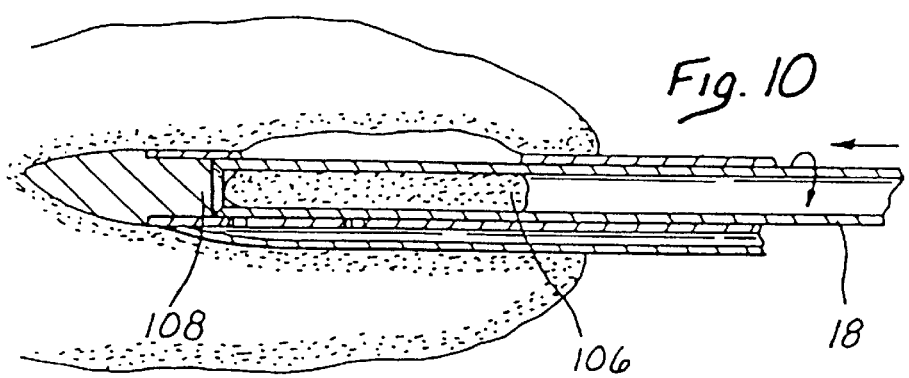
FIG. 10 is an enlarged cross-sectional view similar to FIG. 7, illustrating the simultaneous rotation and distal advancement of the cutter to cut off a tissue sample.
Figure 11:
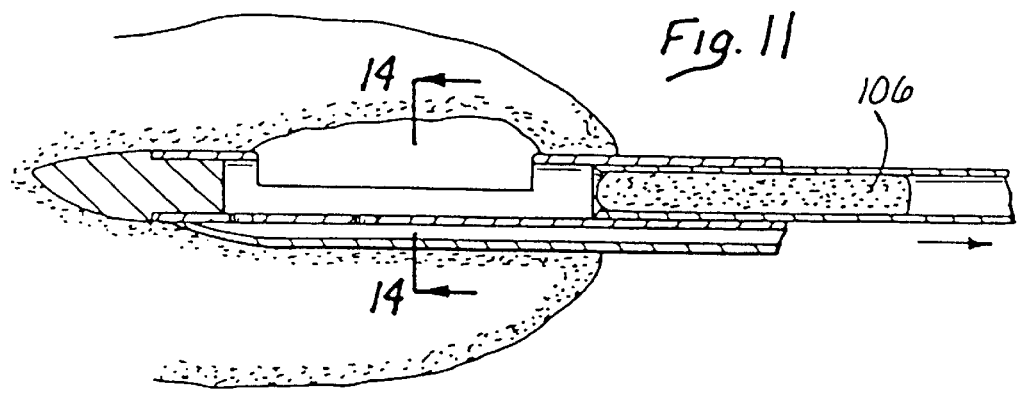
FIG. 11 is an enlarged cross-sectional view similar to FIG. 7, illustrating the proximal withdrawal of the cutter with the tissue sample contained therein.
Figure 12:
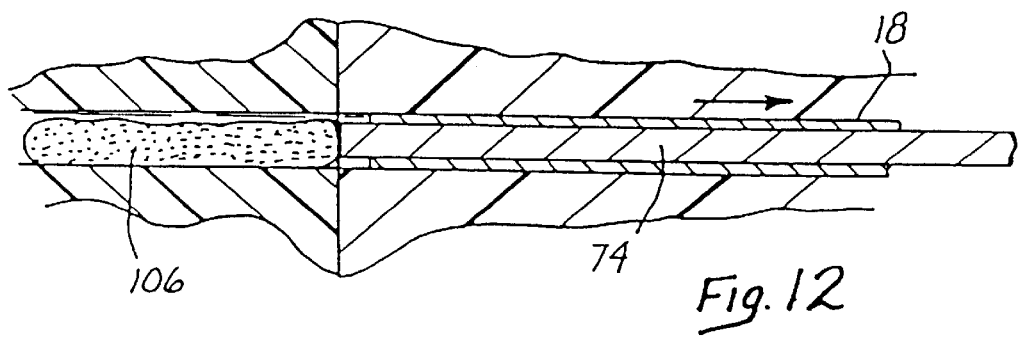
FIG. 12 is an enlarged cross-sectional view of the interface between the proximal end of the tissue cassette and the tissue cassette housing, showing the operation of the knock-out pin to retain the tissue sample in the tissue cassette as the cutter is withdrawn proximally.

Once the tissue is fully prolapsed into the notch 24, as shown in FIG. 9, the prolapsed tissue sample 106 is severed from the main tissue mass by the advancement of the cannular inner cutter 18 (FIG. 11), actuated automatically at the appropriate time by the control unit 72, past the notch 24, to thereby sever the prolapsed tissue sample from the main tissue mass. The biopsy device power and control unit 72 may also operate the cutter drive motor 56 to rotate the cutter gear 50 to thereby rotate the cutter as desired to assist in severing the tissue sample 106. After being severed from the tissue mass, the tissue sample is packed into the inner cutter as the inner cutter moves forward against the needle pin 108, and rests inside the inner cutter 18, as illustrated in FIGS. 10 and 11. The inner cutter 18, containing the tissue sample 106, is then withdrawn, as illustrated in FIG. 11. The tissue sample is held in the inner cutter 18 as it is withdrawn proximally toward the probe housing 22, by friction with the inner walls of the cannula Suction created by the vacuum source 27 can also be used to retain the sample.

As the inner cutter 18 is withdrawn through the probe housing 22, the tissue sample 106 is deposited into a desired receptacle, such as a tissue cassette, by means of the tubular knock-out pin 74, the distal end of which preferably stops the tissue sample within a tissue containment chamber, as is more fully described in the related application Ser. No. 08/217,246.

An important feature of this invention is that control of the linear and rotational movement of the inner cutter 18 and the rotational movement of the outer needle 16, as well as of the vacuum source for aspirating the notch 24 may be accomplished automatically using the control system illustrated in FIGS. 18 and 19. In previous biopsy devices of this type, the inner cutter, outer needle, and vacuum source have all been manually controlled, once the piercing tip of the outer needle has been located at the target lesion using an automatic control system like that illustrated in FIGS. 18 and 19 as described above.

An alternative control system scheme to that shown in FIG. 18 is illustrated in FIG. 19, wherein all of the elements of the system are identical to those shown in FIG. 18, and thus are designated by identical reference numerals, followed by a "b". However, what is different about the system 92b is that the processor 100b is programmed to automatically calculate the points from which tissue samples should be taken in order to effectively sample the entire lesion 90b, rather than having the points 112 denoted manually by the user, as in the FIG. 18 embodiment. Thus, all that a user need do in the FIG. 19 scheme is to drag the cursor across the region 90b desired to be sampled, thereby shading the region, as shown in the drawing. The coordinates of the shaded region are then relayed to the processor 100b, which in turn calculates the number and location of samples within the shaded region necessary to effectively sample the entire region. The coordinates of these calculated points are then transmitted to the controller 102b which instructs the biopsy device power and control unit to actuate the appropriate drive motors in the appropriate sequence to obtain the tissue samples at each of the calculated points, in the same manner as in the FIG. 18 embodiment.

Figure 13:
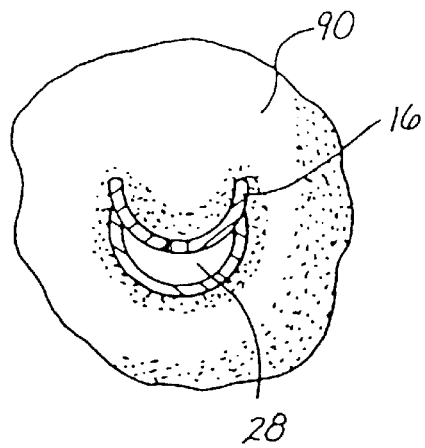
FIG. 13 is a cross-sectional view taken along lines 13—13 of FIG. 9.
Figure 14:
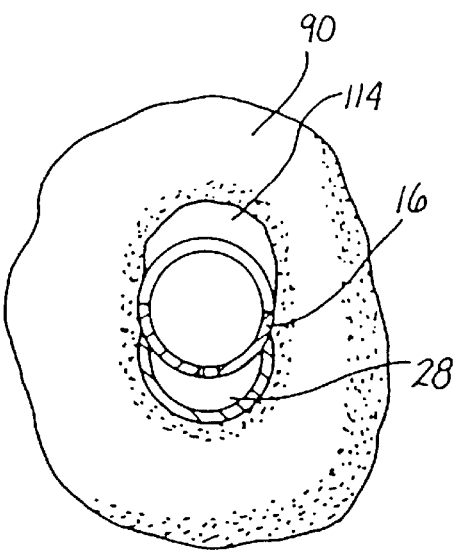
FIG. 14 is a cross-sectional view taken along lines 14—14 of FIG. 11.
Figure 15:
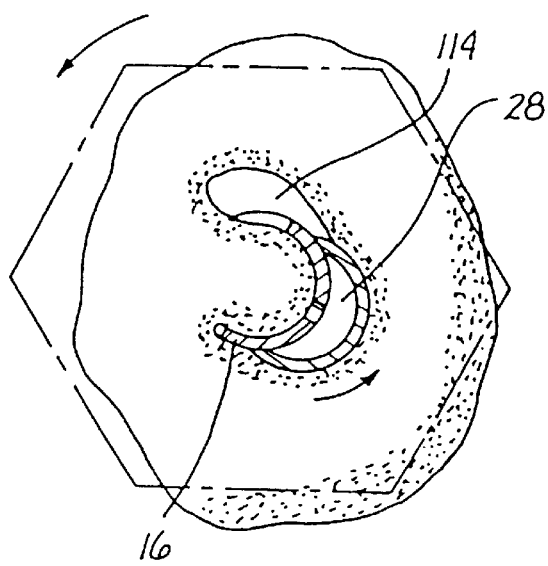
FIG. 15 is a cross-sectional view similar to FIG. 13, wherein the outer needle and inner cutter have been rotated approximately 90 degrees counterclockwise to take a second tissue sample.

FIGS. 13–16 illustrate a procedure wherein four tissue samples from four different points 112 (FIG. 18) or, alternatively, from four different points calculated by the processor 102b (FIG. 19), may be acquired from four different angular positions of the notch 24 and retrieved without removing the hollow outer piercing needle 16 and the notch 24 from the lesion 90. Furthermore, if desired, the integrity of each sample may be preserved and a record of the location from which each of the four samples is acquired may be created by storing the samples in individual sample containment chambers (not shown). FIG. 13 is a cross-sectional view along lines 13—13 of FIG. 9, which illustrates preparations for the taking of a firt sample 106 (FIG. 10) with the needle 16 and associated vacuum lumen 28 angularly oriented so that the notch 24 is in an upright position within the lesion 90. FIG. 14 is a cross-sectional view along lines 14—14 of FIG. 11, wherein the needle 16 is angularly oriented in the same position as in FIG. 13, after the tissue sample has been removed. The void 114 represents the location from which the sample was taken. FIG. 15 shows the needle assembly as illustrated in FIGS. 13 and 14, but where the notch orientation driving mechanism has been used to rotate the needle 16 approximately 90 degrees counterclockwise. A second sample is to be taken from this angular location.

Figure 16:
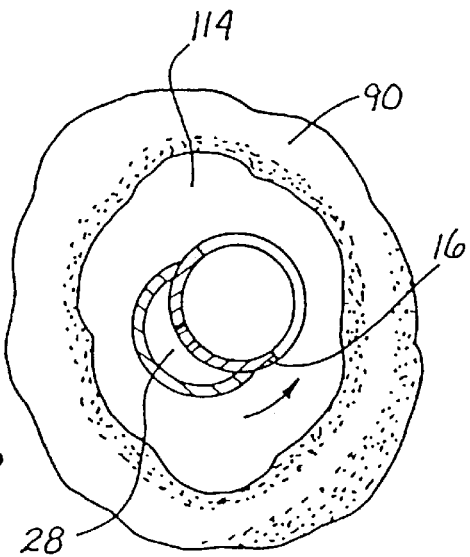
FIG. 16 is a cross-sectional view similar to FIG. 14, wherein the outer needle and inner cutter have been rotated approximately 300 degrees counterclockwise, and a fourth tissue sample has been taken.

Finally, FIG. 16 is yet another similar view, wherein the needle 16 has been rotated by the notch orientation driving mechanism approximately 300 degrees counterclockwise from the original orientation shown in FIGS. 13 and 14 (it should, however, be noted that the invention permits samples to be taken from any angular orientation between 0 and 360 degrees). A sample has already been taken from this location, as depicted in the drawing, as well as from the 180 degree orientation, so that the void 114 now extends entirely about the needle assembly and four tissue samples have been removed.

While this invention has been described with respect to various specific examples and embodiments, it is to be understood that the invention is not limited thereto and that it can be variously practiced within the scope of the following claims.

What is claimed is:

1. An automatic biopsy device, comprising:
    a first elongate cannula having a distal end for entering tissue and a notch located proximally of said distal end for receiving a portion of the tissue which is positioned adjacent to said notch;
    a second elongate cannula disposed coaxially with said first cannula, said second cannula being slidable along the first cannula for cutting the portion of tissue protruding into said notch when said second cannula slides past said notch, thereby depositing the portion of cut tissue within said first elongate cannula proximal to said first cannula distal end;
    a first driving mechanism for rotationally driving said first cannula about its longitudinal axis, so that said notch may be rotated to any desired orientation for sampling tissue from different locations about said first cannula;
    a second driving mechanism for moving said second cannula relative to said first cannula;
    a monitor having a screen for displaying a target lesion site to a user;
    a processor for receiving instructions from said user regarding regions of said target lesion from which tissue samples are to be taken and for generating instructions responsive to the instructions from said user in order to execute obtainment of tissue samples from said regions; and
    a controller for receiving the instructions generated by said processor and for automatically controlling said first driving mechanism to rotate said notch to a desired orientation for obtaining a tissue sample and said second driving mechanism to move said second cannula to cut said tissue sample so that it is deposited within said first cannula.

2. An automatic biopsy device as recited in claim 1, wherein said first elongate cannula comprises an outer hollow piercing needle and said second elongate cannula comprises an inner cutter.

3. An automatic biopsy device as recited in claim 1, and further comprising a housing for containing said first and second driving mechanisms, said housing being attached to a punction arm for moving said housing responsive to control instructions from said processor.

4. An automatic biopsy device as recited in claim 3, wherein said punction arm includes a linear motor on which said housing is mounted and the first cannula extends from said housing, the distal end of the first cannula being positionable in a desired location with respect to said target lesion by movement of said linear motor.

5. An automatic biopsy device as recited in claim 4, wherein said linear motor moves rotationally and axially to position the distal end of the first cannula.

6. An automatic biopsy device as recited in claim 3, and further comprising:
    a punction arm power and control unit for receiving instructions from said controller and for driving said punction arm to move said housing; and
    a biopsy device power and control unit for receiving instructions from said controller and for driving said first and second driving mechanisms to rotationally move said first cannula and to rotationally or axially move said second cannula.

7. An automatic biopsy device as recited in claim 6, wherein said punction arm is driven to rotationally or axially move said housing.

8. An automatic biopsy device as recited in claim 3, wherein said first driving mechanism comprises a notch orientation drive system including:
    a notch orientation motor; and
    a notch orientation drive gear rotatably driven by said notch orientation motor.

9. An automatic biopsy device as recited in claim 8, wherein said first driving mechanism further comprises:
    a power/control cable for providing electrical power and control signals to said notch orientation motor from a biopsy device power and control unit;
    a primary notch orientation gear engaged with and rotatably driven by said notch orientation drive gear and being attached to one end of a rotatable shaft;
    a secondary notch orientation gear attached to a second end of said shaft, and being rotatable responsive to rotation of said shaft; and
    a notch orientation gear fixedly attached about said first cannula, said notch orientation gear being engaged with and rotatably driven by said secondary notch orientation gear to rotate said first cannula responsive to commands from said biopsy device power and control unit.

10. An automatic biopsy device as recited in claim 3, wherein said second driving mechanism comprises:
    a carriage assembly through which said second cannula extends axially;
    a cutter drive motor;

a first power/control cable for providing electrical power and control signals to said cutter drive motor from a biopsy device power and control unit;

a cutter power gear rotatably driven by said cutter drive motor;

a cutter gear disposed in said carriage assembly and engaged with and rotatably driven by said cutter power gear, said cutter gear being fixedly attached about said second cannula to rotate said second cannula responsive to commands from said biopsy device power and control unit;

an axial drive engaged with a lower portion of said carriage assembly and adapted to drive said carriage assembly forwardly or rearwardly in an axial direction;

an axial drive motor for rotatably driving said axial drive; and a second power/control cable for providing electrical power and control signals to said axial drive motor from said biopsy device power and control unit.

11. An automatic biopsy device as recited in claim 1, and further comprising:

a source of vacuum pressure for supplying a vacuum pressure to aspirate said notch and thereby draw tissue into said first cannula proximally of said distal end;

wherein said controller is adapted to control said source of vacuum pressure so that the notch is aspirated as desired.

12. An automatic biopsy device as recited in claim 1, and further comprising a user input device for defining, on said monitor screen, portions of said target lesion site from which tissue samples are to be taken, and thereby providing said instructions to the processor.

13. An automatic biopsy device as recited in claim 12, wherein said monitor screen has a movable cursor thereon and said portions are defined by dragging said cursor through said target region to shade the portions, whereupon the processor calculates necessary points from which tissue samples must be taken to effectively sample all of the shaded portions.

14. An automatic biopsy device as recited in claim 12, wherein said monitor screen has a movable cursor thereon and said portions are defined by dragging said cursor to a plurality of desired points within the target region and clicking on the desired points, thereby instructing the processor to obtain a tissue sample from each desired point in order to effectively sample the entire target region.

15. An automatic biopsy device as recited in claim 1 wherein said first cannula may receive and process a plurality of tissue samples sequentially without retraction from the target lesion.

16. An automatic biopsy device as recited in claim 1, wherein said monitor and said processor comprise elements of a computer system.

17. An automatic biopsy device as recited in claim 15, wherein said controller comprises a further element of said computer system.

18. An automatic biopsy device as recited in claim 1, wherein said second driving mechanism axially moves said second cannula relative to the first cannula.

19. An automatic biopsy device, comprising:

a hollow needle having a distal end and a tissue receiving notch;

a cutter having a sharpened distal end and disposed coaxially within said hollow needle;

a first driver for rotating said hollow needle to orient said tissue receiving notch in a desired radial orientation;

a second driver for axially moving said cutter so that it is slidable along the hollow needle for cutting tissue protruding into said notch; and a processor for receiving instructions from a user related to desired portions of a target lesion to be sampled and instructing a controller to automatically control each of said first and second drivers to move the hollow needle and the cutter in order to obtain the desired tissue lesion portions.

20. An automatic biopsy device as recited in claim 19, and further comprising a third driver for rotationally moving said cutter.

21. A method of controlling an automatic biopsy device said device comprising a first elongate cannula having a distal end for entering tissue and a tissue-receiving notch, and a second elongate cannula having a sharpened distal end and disposed coaxially with the first cannula, the method comprising:

a) providing instructions as to the portions of said lesion from which tissue samples are desired by denoting on a computer monitor screen displaying a target lesion said portions;

b) transmitting said instructions to a processor;

c) processing the instructions and transmitting instructions from said processor to a controller; and d) using the controller to automatically drive said first cannula to rotate to a desired notch position and to automatically drive said second cannula to cut tissue protruding into said notch, thereby obtaining a tissue sample.

22. The method as recited in claim 21, wherein steps a) through d) are repeated to obtain an additional tissue sample.

23. The method as recited in claim 21, wherein steps c) and d) are repeated to obtain an additional tissue sample.

24. The method as recited in claim 21, wherein step a) is performed by manipulating a user input device to shade said portions on said monitor screen.

25. The method as recited in claim 24, wherein step c) includes calculating particular points within said shaded portions from which tissue samples must be taken to effectively sample the shaded portions, and transmitting the coordinates of said particular points to said controller.

26. The method as recited in claim 21, wherein step a) is performed by manipulating a user input device to denote specific points on said monitor screen from which tissue samples should be taken to effectively sample the target lesion.

27. The method as recited in claim 21, wherein step c) includes transmitting the coordinates of said specific points to said controller.

* * * * *